United States Patent
Osada et al.

(10) Patent No.: US 10,161,883 B2
(45) Date of Patent: Dec. 25, 2018

(54) WAFER INSPECTION METHOD AND WAFER INSPECTION APPARATUS

(71) Applicant: SUMCO CORPORATION, Tokyo (JP)

(72) Inventors: Tatsuya Osada, Tokyo (JP); Masahiko Egashira, Tokyo (JP); Tomokatsu Uchino, Tokyo (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 15/757,856

(22) PCT Filed: Aug. 3, 2016

(86) PCT No.: PCT/JP2016/003585
§ 371 (c)(1),
(2) Date: Mar. 6, 2018

(87) PCT Pub. No.: WO2017/043012
PCT Pub. Date: Mar. 16, 2017

(65) Prior Publication Data
US 2018/0328859 A1    Nov. 15, 2018

(30) Foreign Application Priority Data
Sep. 10, 2015   (JP) .................................. 2015-178699

(51) Int. Cl.
*G01N 21/95* (2006.01)
*G01N 21/64* (2006.01)

(52) U.S. Cl.
CPC ..... *G01N 21/9501* (2013.01); *G01N 21/6489* (2013.01)

(58) Field of Classification Search
CPC .................. G01N 21/9501; G01N 21/6489
USPC ................. 356/237.1–237.6, 239.1–239.8
See application file for complete search history.

(56) References Cited

U.S. PATENT DOCUMENTS

| 4,449,818 A | 5/1984 | Yamaguchi et al. |
| 8,411,263 B2 | 4/2013 | Uchino et al. |

FOREIGN PATENT DOCUMENTS

| JP | S57-132044 A | 8/1982 |
| JP | H2-31141 A | 2/1990 |
| JP | H2-213710 A | 8/1990 |
| JP | H3-73831 A | 3/1991 |
| JP | 2000-193434 A | 7/2000 |
| JP | 2010-103275 A | 5/2010 |
| TW | 200951430 A | 12/2009 |
| WO | 2014/210195 A1 | 12/2014 |

OTHER PUBLICATIONS

U.S. Appl. No. 15/765,349 to Tatsuya Osada et al., filed Apr. 2, 2018.

(Continued)

*Primary Examiner* — Tri T Ton
(74) *Attorney, Agent, or Firm* — Greenblum & Bernstein, P.L.C.

(57) ABSTRACT

Provided is a wafer inspection method capable of examining whether pits are formed in wafer surfaces. The wafer inspection method includes the steps of: choosing defects of a wafer using a first optical system; selecting potential pits from the chosen defects; and classifying the potential pits into pits and defects other than the pits using a second optical system.

6 Claims, 7 Drawing Sheets

(56) References Cited

OTHER PUBLICATIONS

International Search Report issued in WIPO Patent Application No. PCT/JP2016/003585, dated Oct. 18, 2016.
Office Action issued in Taiwan family member Patent Appl. No. 105124574, dated Jun. 13, 2017, along with an English translation thereof.
International Preliminary Report on Patentability issued in WIPO Patent Application No. PCT/JP2016/003585, dated Mar. 13, 2018, along with an English translation thereof.

WAFER INSPECTION METHOD AND WAFER INSPECTION APPARATUS

TECHNICAL FIELD

This disclosure relates to a wafer inspection method and a wafer inspection apparatus for examining whether defects are formed wafer surfaces. This disclosure relates in particular to a wafer inspection method capable of examining whether pits are formed in wafer surfaces.

BACKGROUND

In terms of enhancing yield and reliability of semiconductor device manufacturing processes, inspection techniques for detecting defects in the surfaces of wafers used as substrates for semiconductor devices have increasingly become very important. Ideally, no defects are formed in wafer surfaces; however, some defects are negligible in terms of device characteristics and yield in device manufacturing. Therefore, the wafer surfaces are examined based on predetermined criteria and the wafers are determined whether they are conforming products or defective products.

In this specification, crystal defects, flaws, foreign matters, etc. in wafer surfaces are collectively referred to as "defects". The defects include pits, crystal defects such as COPs, and unevenly polished portions and scratches formed due to machining as well as particles which are foreign matters attached to wafer surfaces. Further, the term "wafer surfaces" herein refers to both a main surface on the front side of a wafer and a main surface on the rear side thereof, and is distinguished from only a surface on one side.

Conventionally, using a light point defect (LPD) inspection apparatus, wafer inspection is performed in which wafer surfaces having been finished by mirror polishing are scanned with laser light thereby detecting scattered light resulted from particles, scratches, and the like in the surfaces. Further, in order to determine the presence and absence of defects that are hardly determined by an LPD inspection apparatus, appearance inspection is also performed in which wafer surfaces are examined by visual observation. Since appearance inspection is an organoleptic test, variation in the determination depending on inspectors cannot be avoided, and it takes time for inspectors to master the examination technique. Therefore, there is a demand for establishing an objective inspection method and an automatic inspection method.

To address the above challenge, we have previously proposed in JP 2010-103275 A (PTL 1), as a wafer inspection method, a method of properly evaluating wafers without appearance inspection especially focusing on defects on the rear surface side of the wafer surfaces. Specifically, the method is a method of evaluating the rear surface of a wafer, including: a mapping step of consecutively taking partial images of the rear surface of a wafer in the circumference direction of the wafer and synthesizing the taken partial images to compose a full image of the rear surface of the wafer; and a differentiation step of differentiating the full image to create a differentiated image of the rear surface of the wafer, wherein the wafer is evaluated by detecting unevenly polished portions, haze, scratches, and particles based on the full image or the differentiated image.

CITATION LIST

Patent Literature

PTL 1: JP 2010-103275 A

SUMMARY

Technical Problem

Figure 1A:
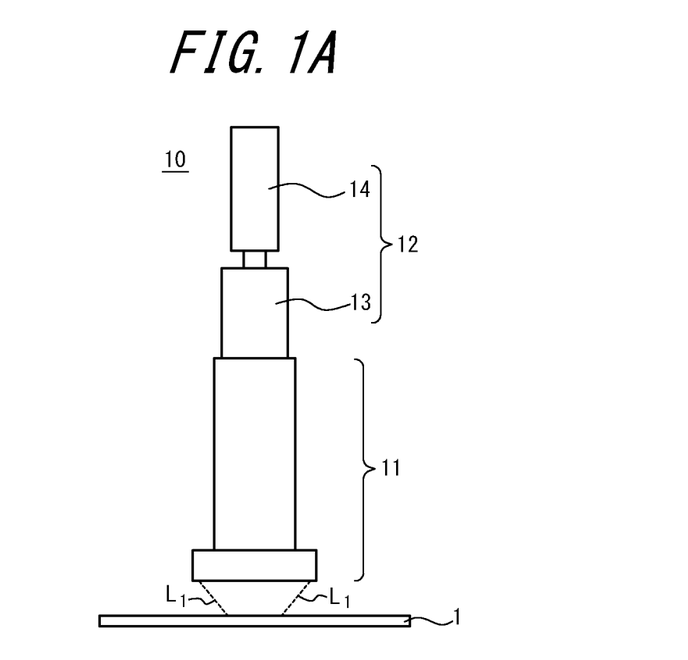
FIG. 1A is a schematic view of the whole first optical system 10 and FIG. 1B is a schematic view illustrating incident light $L_1$ from the first optical system 10 and scattered light $L_2$.
Figure 1B:
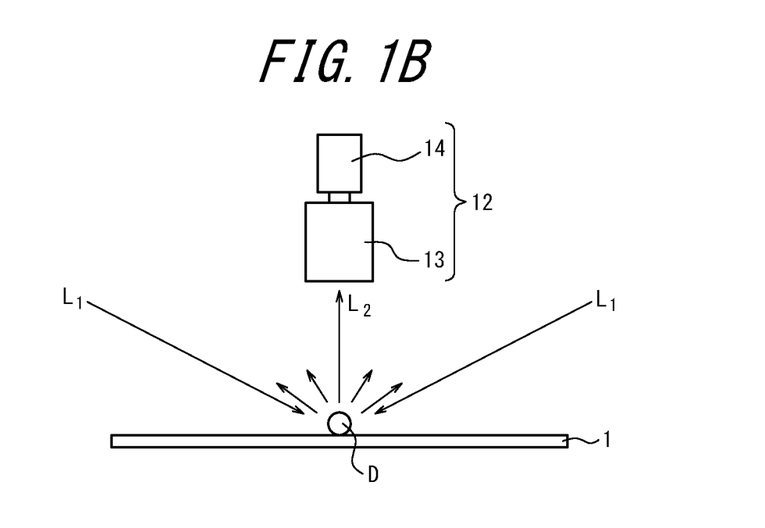

Here, the above-mentioned optical system for creating a full image of the wafer surfaces is described with reference to FIGS. 1A and 1B. FIG. 1B depicts the major part of FIG. 1A for illustrating irradiation light $L_1$ emitted by an annular fiber optic illuminator 11 and reflected light (scattered light) $L_2$. A first optical system 10 includes the annular fiber optic illuminator 11 and a first light receiving unit 12. The first light receiving unit is composed of, for example, a telecentric lens 13 and a light receiving unit 14 including a CCD camera. The annular fiber optic illuminator includes a super high pressure mercury lamp. The irradiation light $L_1$ emitted by the annular fiber optic illuminator 11 enters a wafer 1 at an angle of for example 20° to the wafer plane and becomes the scattered light $L_2$ upon colliding with a defect D present in the surface of the wafer 1. The first light receiving unit 12 takes an image upon receiving perpendicular scattered light of the scattered light $L_2$, thereby collecting the information of the position of the first optical system 10 and the brightness information thereof.

Figure 2A:
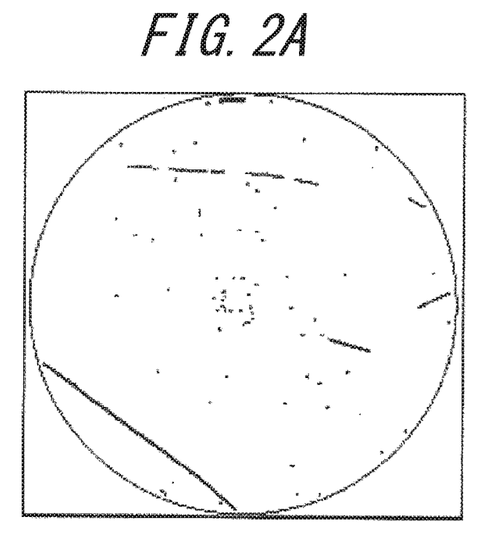
FIG. 2A is an example of a full image of wafer defects that is obtained by the first optical system 10 and FIG. 2B is an example of a full image of wafer defects that is obtained by a commercially available LPD inspection apparatus.
Figure 2B:
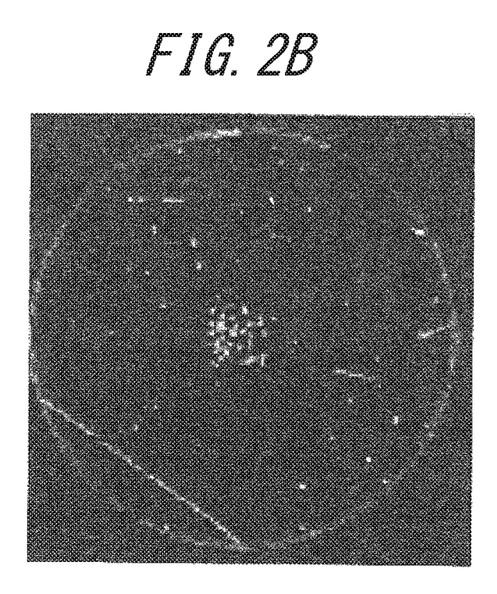

The entire surface of the wafer is scanned by the first optical system 10 and image processing is performed; thus, the full image of the surface of the wafer can be obtained. Note that in order to reduce scanning time, a plurality of first optical systems 10 are usually placed on the front and rear surfaces of a wafer. FIG. 2A illustrates an example of a full image of one surface of a wafer taken by such a first optical system 10, and FIG. 2B is an LPD map obtained by inspecting the same wafer using a commercially available LPD inspection apparatus (SP1 manufactured by KLA-Tencor Corporation). FIGS. 2A and 2B illustrate that scratches, particles, etc. can be detected by either apparatus.

In a wafer inspection method using a conventional wafer inspection apparatus, since it is difficult to identify patterns unique to pits, defects identified as particles would include pits. Relatively large pits such as ones having a major axis or a long side exceeding 20 μm can be identified as pits by appearance inspection by visual observation, and a wafer having no such pits is determined to be a wafer free of pits. However, relatively small pits having a major axis or a long side of 20 μm or less can hardly be identified as pits by appearance inspection due to the limits of visual resolution. Particles would cause damage during wafer suction or wafer transfer; however, wafers with a certain level of particle number or less are used as products. Accordingly, in conventional techniques, wafers having small pits which have been overlooked could be used as products as they are. Note that the term "pits" herein refers to cavity-like defects due to machining or crystal defects, excluding minute defects including for example crystal originated particles (COPs) having a major axis or a long side of 0.2 μm or less.

Even the above relatively small pits would cause problems in increasingly miniaturized semiconductor devices. Specifically, when dicing a wafer after device fabrication, crack damage can be triggered by those pits, which would results in cracking of the wafer. When a wafer is cracked in the dicing step, all devices mounted on the wafer become defective; accordingly, those pits can be critical defects in the device fabrication process. We thus realized the necessity for establishing a method capable of reliably examining whether pits are formed in wafer surfaces.

In view of the above problems, it could be helpful to provide a wafer inspection method and a wafer inspection apparatus which make it possible to examine whether pits are formed in wafer surfaces.

Solution to Problem

With a view to achieving the above objective, we diligently made studies and focused on that recesses and protrusions in wafer surfaces can be identified and pits can be detected using an optical system including an parallel light illuminating light source utilizing the so-called magic mirror theory. However, detecting pits in wafer surfaces all over the wafer surfaces by this optical system takes significant inspection time, which is not realistic in terms of productivity. On the other hand, in an inspection using the above-described first optical system 10, although it is difficult to determine whether a defect is a pit or not, defects that can be pits, i.e., potential pits can be chosen based on the size of the defect, the defect pattern, and the brightness information. The number of defects chosen as potential pits in a wafer having been finished by mirror polishing is approximately several hundreds at most. We discovered that when recesses and protrusions of the total number of potential pits chosen by the first optical system 10 are identified using an optical system utilizing the magic mirror theory, the above potential pits can be classified whether they are pits or not, and the inspection time is acceptable in terms of productivity. This discovery led to this disclosure. This disclosure is based on the above findings and studies and we propose the following features.

A wafer inspection method according to this disclosure includes the steps of: choosing defects of a wafer by scanning the wafer by a first optical system including an annular fiber optic illuminator and a first light receiving unit which is placed perpendicular to a surface of the wafer while the first optical system is used to irradiate a certain position on the surface of the wafer and receive perpendicular scattered light resulted from the defects of the wafer, thereby collecting information of brightness at the certain position; selecting potential pits from the chosen defects; and classifying the potential pits into pits and the defects other the pits using a second optical system including a parallel light illuminating light source and a second light receiving unit which is placed to be tilted relative to the surface of the wafer by imaging the potential pits with every change of the focus position of the second optical system, the classification being performed based on light and dark patterns of the imaged potential pits obtained by the change of the focus position.

In the classifying step, the classification is preferably performed by identifying, as pits, potential pits which are imaged darkly when the focus position is in a reverse position and are imaged brightly when the focus position is in a forward position.

It is preferred that the potential pits include particles.

Preferably, in the selecting step, defects having a major axis or a long side of 20 μm or less are selected as the potential pits from the defects.

The wafer is preferably a silicon wafer subjected to mirror polishing.

A wafer inspection apparatus according to this disclosure includes: a first optical system including an annular fiber optic illuminator and a first light receiving unit which is placed perpendicular to a surface of a wafer; a second optical system including a parallel light illuminating light source and a second light receiving unit which is placed to be tilted relative to the surface of the wafer; a first scanning unit scanning the surface of the wafer in parallel by the first optical system; a second scanning unit scanning the surface of the wafer in parallel by the second optical system, with the tilt of the second optical system being maintained; and a control unit controlling the first optical system, the second optical system, the first scanning unit, and the second scanning unit, wherein the control unit controls the first optical system to irradiate a certain portion of the surface of the wafer, makes the first light receiving unit receive perpendicular scattered light resulted from defects of the wafer; controls the first scanning unit to scan the wafer with the first optical system thereby collecting brightness information of the perpendicular scattered light while collecting brightness information of the entire surface of the wafer; and chooses defects of the wafer, selects potential pits from the chosen defects, controls the second optical system and the second scanning unit to change the focus position of the second optical system thereby imaging the potential pits, and classifies the potential pits into pits and defects other than the pits based on light and dark patterns of the imaged potential pits obtained by the change of the focus position of the second optical system.

Advantageous Effect

We provide a wafer inspection method and a wafer inspection apparatus which make it possible to examine whether pits are formed in wafer surfaces.

BRIEF DESCRIPTION OF THE DRAWINGS

In the accompanying drawings:

FIGS. 1A and 1B are schematic views illustrating a first optical system 10 of one embodiment of this disclosure, in which

FIGS. 2A and 2B are full images of wafer defects detected in Conventional Example, in which

FIGS. 5A to 5C are schematic views illustrating the second optical system 20, in which

FIGS. 6A to 6C are examples of a pit which can be identified by a wafer inspection method according to one embodiment of this disclosure, in which

DETAILED DESCRIPTION

Figure 3:
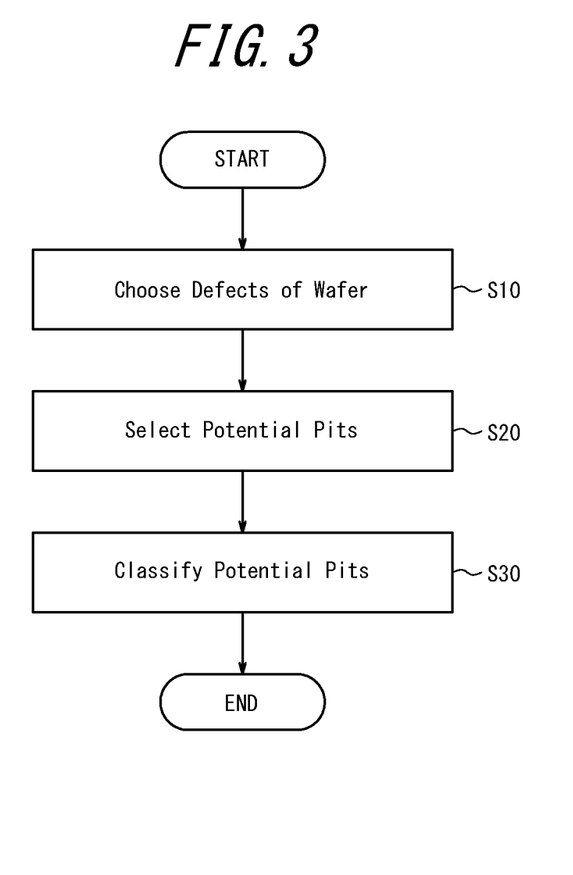
FIG. 3 is a flowchart of a wafer inspection method according to one embodiment of this disclosure.
Figure 7:
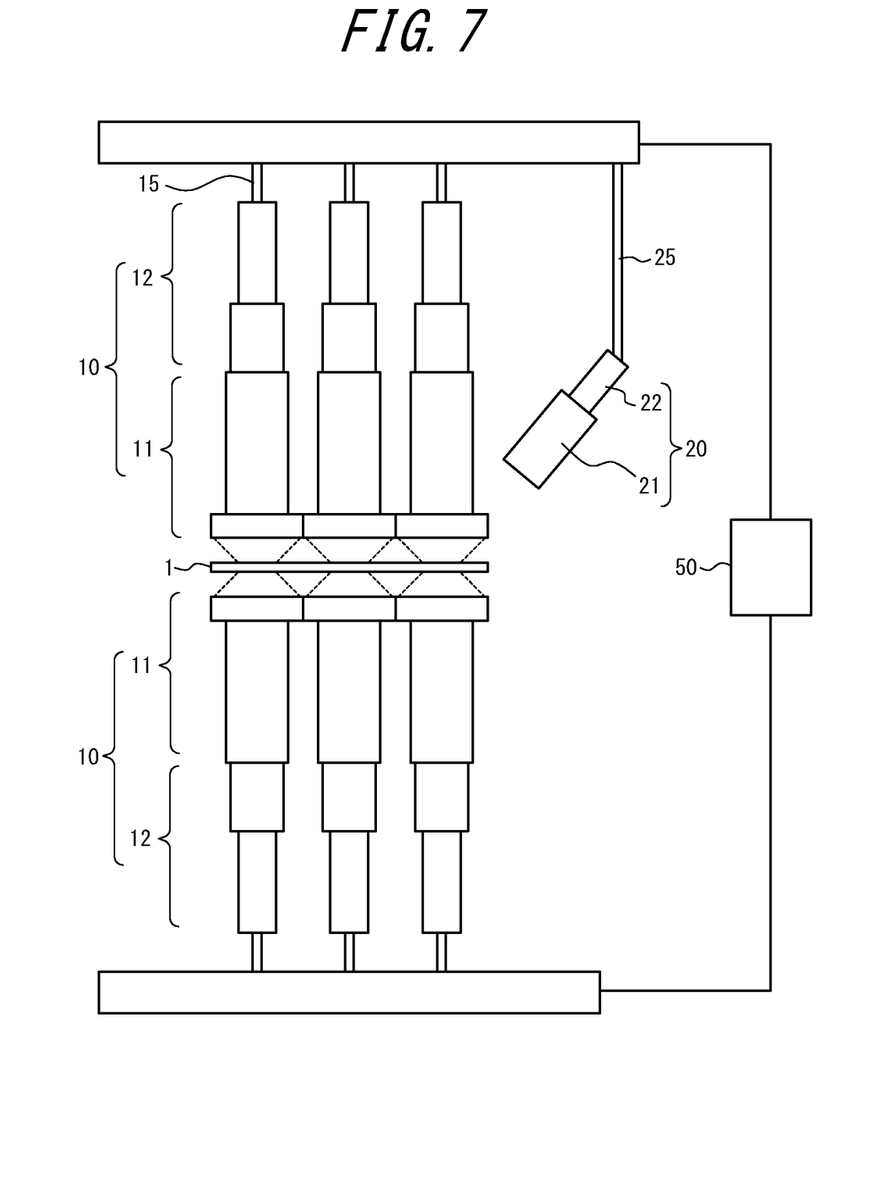
FIG. 7 is a schematic view of a wafer inspection apparatus 100 according to one embodiment of this disclosure.

Embodiments of this disclosure will now be described with reference to the drawings. FIG. 3 is a flowchart of a wafer inspection method according to one embodiment of this disclosure. In accordance with the flowchart, the presence and absence of pits are determined using both the above-mentioned first optical system 10 in FIGS. 1A and 1B and the second optical system 20 to be described with reference to FIG. 4. FIG. 7 is a schematic view of the wafer inspection apparatus 100 according to one embodiment of this disclosure. The wafer inspection apparatus 100 has the above first optical system 10 and the second optical system 20.

(Wafer Inspection Method)

As illustrated in FIG. 3 and FIGS. 1A and 1B, 4, and 7, a wafer inspection method according to one embodiment of this disclosure includes: Step S10 of choosing defects of a wafer 1 by scanning the wafer 1 by a first optical system 10 including an annular fiber optic illuminator 11 and a first light receiving unit 12 which is placed perpendicular to a surface of the wafer 1 while the first optical system 10 is used to irradiate a certain position on the surface of the wafer 1 and receive perpendicular scattered light resulted from the defects of the wafer 1, thereby collecting information of brightness at the certain position; Step S20 of selecting potential pits from the chosen defects; and Step S30 of classifying the potential pits into pits and the defects other the pits using a second optical system 20 including a parallel light illuminating light source 21 and a second light receiving unit 22 which is placed to be tilted relative to the surface of the wafer 1 by imaging the potential pits with every change of the focus position of the second optical system 20, the classification being performed based on light and dark patterns of the imaged potential pits obtained by the change of the focus position. These steps will be sequentially described in detail below.

First, in Step S10, defects of the wafer 1 are chosen. This step can be performed in the same manner as a conventional technique. The above-mentioned first optical system 10 in FIGS. 1A and 1B is used to irradiate a certain position of a surface of the wafer 1 and receive perpendicular scattered light resulted from defects of the wafer 1, thereby collecting information of brightness at the certain position (hereinafter referred to as "defect information"). The entire surface of the wafer 1 is scanned by the first optical system 10 for the collection, thus obtaining the full information of the defect information. In order to clearly examine the defects, differentiation, filtering, etc. may be performed on the defect information as necessary. Thus, the defect information of the defects present in the surface of the wafer 1 is chosen with their positions from the defect information comprehensively irrespective of the classification of the defects. A full image obtained by image processing of the resulting defect information of one surface is for example FIG. 2A as described above, and a full image of the defect information of the opposite surface can also be obtained in the same manner. As described above and as will be described with reference to FIG. 7, placing a plurality of the first optical systems 10 on both surfaces of the wafer (three each on both surfaces in FIG. 7) allows quick collection of the defect information.

In subsequent Step S20, potential pits are selected from the defects chosen in Step S10. According to our studies, for the defect information obtained by the above first optical system 10, the size of pits and brightness pattern calculated from the position information and the brightness information (i.e., defect information) represent approximately the same size and brightness pattern as particles or wedge-shaped flaws introduced by machining. Accordingly, defects conventionally identified as particles or wedge-shaped machining marks in the defect information may include pits. Therefore, the potential pits may include wedge-shaped machining marks as well as particles other than actual pits. In other words, the potential pits can include pits, particles, and wedge-shaped machining marks. Consequently, in this step, in the defect information obtained by the above first optical system 10, defects conventionally identified as particles or wedge-shaped machining marks are treated as potential pits.

Note that the selection of potential pits (for example, identification of particles in the conventional technique in PTL 1) can be performed as follows. Potential pits are defects represented by brightness information consisting of dot-sized spots randomly present in wafer surfaces. In other words, the defect information of spots having a size exceeding a certain threshold value represents for example flaws such as scratches and unevenly polished portions, and defects having the typical size, shape, or brightness pattern can be excluded from potential pits. Accordingly, certain threshold values are set for the size and brightness of the defects based on the defect information differentiated as necessary, so that potential pits can be identified. All the defects identified as potential pits are selected as potential pits to be subjected to classification into pits and defects other than the pits in subsequent Step S30. Since this embodiment is aimed at classifying potential pits into pits and defects other than the pits, the details are omitted. Note however that since scratches, unevenly polished portions, etc. have the respective typical sizes, shapes, and brightness patterns, additional inspection of defects other than pits can be performed by pattern matching based on those characteristics. Further, potential pits can be chosen from defects having a major axis or a long side of 20 µm or less from the defects. Here, when a pit has a rounded shape such as a circular or elliptical shape, the size of the pit is determined by a length of the major axis thereof. Alternatively, when a pit has a substantially polygonal shape, the size of the pit is determined by a length of the longest side thereof. As described above, minute defects such as COPs are excluded from the pits or potential pits. Accordingly, the size of potential pits may be defined to be more than 0.2 µm and 20 µm or less based on the major axis or long side.

Figure 4:
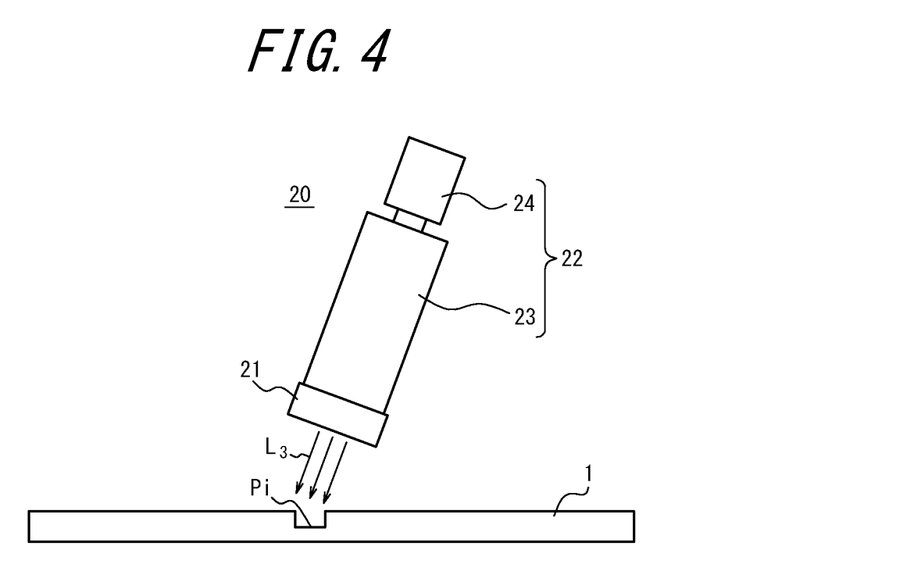
FIG. 4 is a schematic view illustrating a second optical system 20 used in one embodiment of this disclosure.

In subsequent Step S30, the above potential pits are classified into pits and defects other than the pits. Here, this step uses the second optical system 20 including the parallel light illuminating light source 21 and the second light receiving unit 22 utilizing the so-called magic mirror theory. As illustrated in FIG. 4, the second optical system 20 is placed to be tilted relative to a surface of the wafer 1. The parallel light illuminating light source 21 is not limited as long as it can emit parallel light. For example, a blue LED laser can be used. The second light receiving unit 22 includes a magic mirror optical system 23 capable of adjusting the focus position and a light receiving unit 24 including a CCD camera.

Since the second optical system 20 is placed to be tilted, the illuminating light source 21 can emit parallel light $L_3$ angled at a predetermined angle θ (not shown) relative to the surface of the wafer 1. FIG. 4 is a schematic view illustrating irradiating a pit Pi in the surface of the wafer 1 with the parallel light $L_3$. The angle θ formed between the parallel light $L_3$ and the surface of the 1 is not limited as long as the magic mirror theory can be applied. For example, the angle θ is preferably 65° or more and less than 90°, more preferably 70° or more, most preferably 85° or more. When the angle of incidence is excessively large, the scattered light hardly focuses and the S/N ratio can hardly be determined. It should be noted that when the angle θ is 90°, the parallel light $L_3$ emitted is angled perpendicular to the surface of the wafer, which makes it impossible to detect pits.

With the use of the second optical system 20, the focus position of the second optical system 20 is changed to image the above potential pits. Based on light and dark patterns of the imaged potential pits obtained by the change of the focus position, the potential pits are classified into pits Pi and defects other than the pits. Image patterns of light and dark typical of pits Pi can be clearly distinguished from image patterns of defects other than pits Pi (for example, particles Pa) as described below.

Figure 5A:
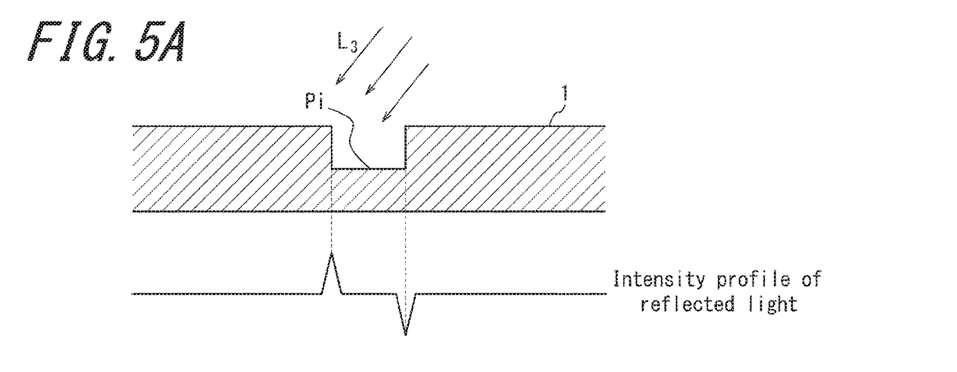
FIG. 5A is a conceptual diagram illustrating irradiating a pit Pi with parallel light $L_3$.
Figure 5B:
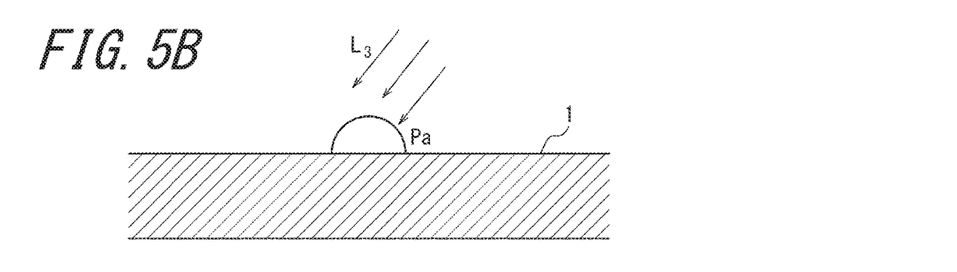
FIG. 5B is a conceptual diagram illustrating irradiating a particle Pa with parallel light $L_3$.

Here, the principle of detecting recesses and protrusions in the surfaces of the wafer 1 using the second optical system 20 will be described in more detail with reference to FIGS. 5A to 5C. In the schematic view illustrated in FIG. 5A, in the case where a pit Pi is irradiated with parallel light $L_3$, when the intensity of light reflected by part of the wafer 1 with no defects is the reference intensity, in the intensity profile of reflected light, the intensity at the rising part (edge portion) of the recess of the pit Pi on the side farther from the illuminating source is higher than the reference intensity. By contrast, the intensity at the rising part (edge portion) of the recess of the pit Pi on the side closer to the illuminating source is lower than the reference intensity. Thus, when the second optical system 20 which detects pits Pi is used, the order of light and dark areas in radial direction in the patterns depends on recesses and protrusions on a measurement object. Recesses and protrusions are detected using this principle. When a pit is as large as can be detected by appearance inspection, the reflection intensity profile as illustrated in FIG. 5A can be clearly obtained. Therefore, when an intensity profile including a peak greater than the reference intensity by more than a predetermined threshold value and a peak less than the reference intensity by more than the above predetermined threshold value is obtained, the intensity profile can be determined as the intensity profile corresponding to a pit Pi. In this embodiment, pits which are not as large as can be detected by appearance inspection are also detected. In such a case, the pits cannot always be clearly identified by only the intensity profile because the signal peaks are buried in noise. Accordingly, the pits are identified utilizing the magic mirror theory described below.

Note that when a potential pit is a particle Pa (FIG. 5B), although depending on the gain of the measurement apparatus, a signal corresponding to the particle Pa is detected at an S/N ratio approximately several hundred times larger than that of the reference intensity. The intensity profile of reflected light is clearly different between a pit Pi and a particle Pa.

Figure 5C:
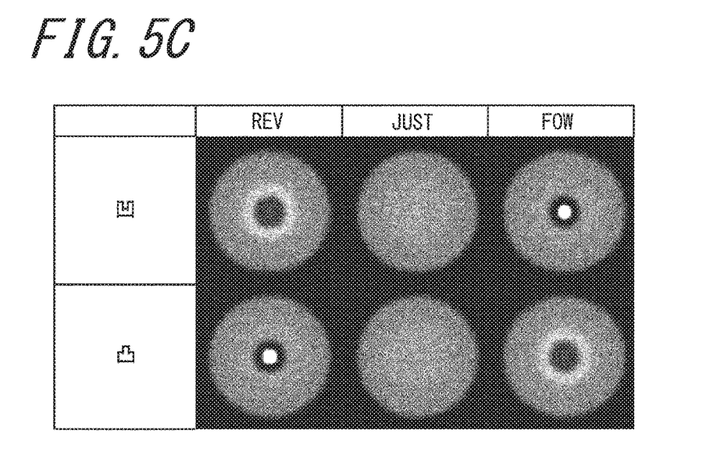
FIG. 5C illustrates examples of processed images of reflected light.

FIG. 5C illustrates examples of image processing of a concave recess and a convex protrusion imaged by the second optical system 20. The pit Pi corresponds to the concave recess in FIG. 5C, and the particle Pa corresponds to the convex protrusion in FIG. 5C. Note that both the recess and the protrusion in this example have a depth (height) of 6 nm. When the focus position of the second optical system (magic mirror optical system) 20 is changed so that a defocused state is established and a REV mode (reverse position defocusing) is set, a protruded shape is observed to be brightly imaged (whereas a recessed shape is darkly imaged). By contrast, in a FOW mode (forward position defocusing), a recessed shape is observed to be brightly imaged (whereas a protruded shape is darkly imaged). The focus position is adjusted as described above and potential pits are imaged so that defects having a recessed shape are selected. Thus, the recessed shapes corresponding to pits Pi can be identified. As described above, a beam of light emitted from the second optical system 20 (magic mirror illuminating optical system) is parallel light (parallel light $L_3$). When a measurement object is irradiated with the light at an angle, light and dark are produced by edge portions. The order of light and dark areas in radial direction in the patterns depends on recesses and protrusions in the measurement object, and the recesses and protrusions are detected using this phenomenon. Thus, defects having a recessed shape in the surface of the wafer 1 are selected utilizing the magic mirror theory. Note that when the focus position is adjusted to JUST position, a recessed shape and a protruded shape cannot be distinguished.

Further, the wafer 1 is preferably a silicon wafer subjected to mirror polishing. When a silicon wafer subjected to mirror polishing is used as described above, the number of defects chosen as potential pits is several hundreds at most, and even if full measurement is performed using the second optical system 20, the increase in the inspection time is limited and acceptable in terms of productivity.

Figure 6A:
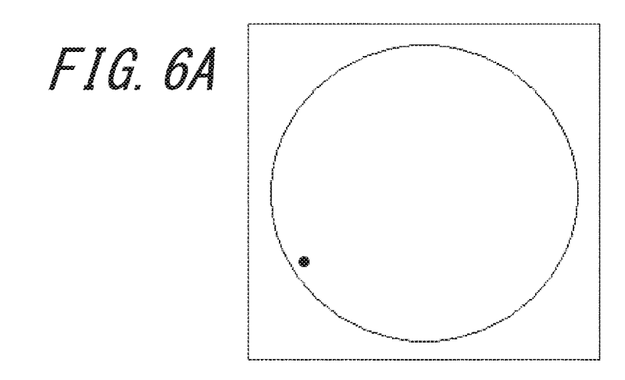
FIG. 6A illustrates the position of the pit in a wafer.
Figure 6B:
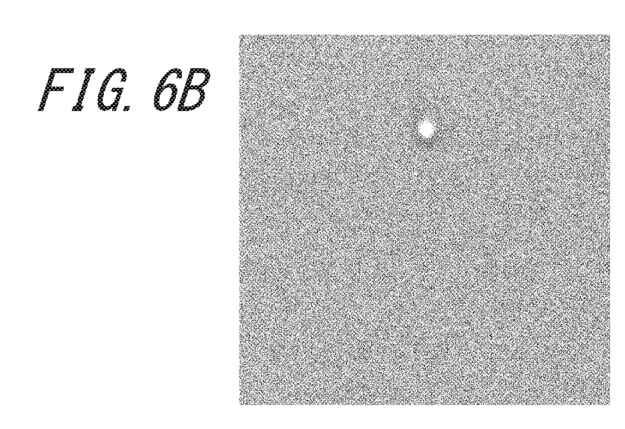
FIG. 6B presents an image of the pit imaged by the first optical system.
Figure 6C:
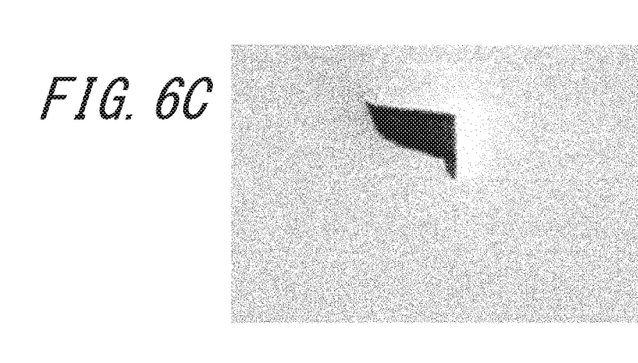
FIG. 6C is a micrograph of the pit.

As an example of a pit which can be observed by a wafer inspection method according to the above embodiment, a pit having a long side with a length of 7 μm present in a surface of a silicon wafer subjected to mirror polishing will be described with reference to FIGS. 6A to 6C. Note that the size of recesses and protrusions which can be identified by visual observation is limited to approximately 20 μm, so that a 7 μm pit which is a recess smaller than the size cannot be identified by appearance examination. This pit corresponds to one at the position in the wafer indicated in FIG. 6A. An image of the pit imaged by the first optical system 10 is as presented in FIG. 6B. Here, the pit is precisely a potential pit since the first optical system is not capable of classification into pits and particles. When this pit was irradiated with parallel light $L_3$ by the second optical system 20, the intensity profile of the reflected light formed a pattern typical of pits; thus, the pit was identified as a pit. The pit was observed under a microscope as illustrated in FIG. 6C. As described above, even relatively small pits conventionally regarded as particles can be accurately determined whether they are pits or not by the wafer inspection method according to this embodiment.

(Wafer Inspection Apparatus)

As schematically illustrated in FIG. 7, the wafer inspection apparatus 100 according to one embodiment of this disclosure has: a first optical system 10 including an annular fiber optic illuminator 11 and a first light receiving unit 12 which is placed perpendicular to a surface of a wafer 1; a second optical system 20 including a parallel light illuminating light source 21 and a second light receiving unit 22 which is placed to be tilted relative to the surface of the wafer 1; a first scanning unit 15 scanning the surface of the wafer 1 in parallel by the first optical system 10; a second scanning unit 25 scanning the surface of the wafer 1 in parallel by the second optical system 20, with the tilt of the second optical system 20 being maintained; and a control unit 50 controlling the first optical system 10, the second optical system 20, the first scanning unit 15, and the second scanning unit 25. The control unit 50 controls the first optical system 10 to irradiate a certain portion of the surface of the wafer, and makes the first light receiving unit receive perpendicular scattered light resulted from defects of the wafer. Further, the control unit 50 controls the first scanning unit 15 to scan the wafer by the first optical system 10 thereby collecting brightness information of the perpendicular scattered light while collecting brightness information of the entire surface of the wafer 1. The control unit 50 also chooses defects of the wafer 1, selects potential pits from the chosen defects, and controls the second optical system 20 and the second scanning unit 25 to change the focus position of the second optical system 20 thereby imaging the potential pits, and classifies the potential pits into pits and defects other than the pits based on light and dark patterns of the imaged potential pits obtained by the change of the focus position of the second optical system. Only one second optical system 20 is illustrated in FIG. 7; the second optical system 20 may be provided on the opposite side of the wafer 1. Alternatively, a plurality of the second optical systems 20 may be provided.

The control unit 50 is implemented by a suitable processor such as a central processing unit (CPU) or an MPU. The control unit 50 may have a storage unit such as a memory or a hard disk. Further, the control unit 50 controls the transmittance of information and instructions between the components of the wafer inspection apparatus 100 and the operation of each unit by executing programs for performing the above wafer inspection method previously stored in the control unit 50. The first scanning unit 15 and the second scanning unit 25 may be composed of an arm connected to respective cameras (light receiving units) of the first optical system 10 and the second optical system 20, a drive stepper motor or a servomotor for actuating the arm, and others.

Although the embodiments of this disclosure have been described above, the embodiments are illustrated only as representative examples, and therefore this disclosure is not limited thereto and may be changed in various manners within the spirit of this disclosure.

INDUSTRIAL APPLICABILITY

We provide a wafer inspection method and a wafer inspection apparatus which make it possible to examine whether pits are formed in wafer surfaces.

REFERENCE SIGNS LIST

1: Wafer
10: First optical system
11: Annular fiber optic illuminator
12: First light receiving unit
15: First scanning unit
20: Second optical system
21: Parallel light illuminating light source
22: Second light receiving unit
25: Second scanning unit
50: Control unit
D: Defect
Pa: Particle
Pi: Pit

The invention claimed is:

1. A wafer inspection method comprising:
choosing defects of a wafer by scanning the wafer by a first optical system including an annular fiber optic illuminator and a first light receiving unit which is placed perpendicular to a surface of the wafer while the first optical system is used to irradiate a certain position on the surface of the wafer and receive perpendicular scattered light resulted from the defects of the wafer, thereby collecting information of brightness at the certain position;
selecting potential pits from the chosen defects; and
classifying the potential pits into pits and the defects other the pits using a second optical system including a parallel light illuminating light source and a second light receiving unit which is placed to be tilted relative to the surface of the wafer by imaging the potential pits with every change of the focus position of the second optical system, the classification being performed based on light and dark patterns of the imaged potential pits caused due to the change of the focus position.

2. The wafer inspection method according to claim 1, wherein in the classifying, the classification is performed by identifying, as pits, potential pits which are imaged darkly when the focus position is in a reverse position and are imaged brightly when the focus position is in a forward position.

3. The wafer inspection method according to claim 1, wherein the potential pits include particles.

4. The wafer inspection method according to claim 1, wherein in the selecting, defects having a major axis or a long side of 20 μm or less are selected as the potential pits from the defects.

5. The wafer inspection method according to claim 1, wherein the wafer is a silicon wafer subjected to mirror polishing.

6. A wafer inspection apparatus comprising:
a first optical system including an annular fiber optic illuminator and a first light receiving unit which is placed perpendicular to a surface of a wafer;
a second optical system including a parallel light illuminating light source and a second light receiving unit which is placed to be tilted relative to the surface of the wafer;
a first scanning unit scanning the surface of the wafer in parallel by the first optical system;
a second scanning unit scanning the surface of the wafer in parallel by the second optical system, with the tilt of the second optical system being maintained; and
a control unit controlling the first optical system, the second optical system, the first scanning unit, and the second scanning unit,
wherein the control unit controls the first optical system to irradiate a certain portion of the surface of the wafer, makes the first light receiving unit receive perpendicular scattered light resulted from defects of the wafer; controls the first scanning unit to scan the wafer with the first optical system thereby collecting brightness information of the perpendicular scattered light while collecting brightness information of the entire surface of the wafer; and chooses defects of the wafer, selects potential pits from the chosen defects, controls the second optical system and the second scanning unit to change the focus position of the second optical system thereby imaging the potential pits, and classifies the potential pits into pits and defects other than the pits based on light and dark patterns of the imaged potential pits caused due to the change of the focus position of the second optical system.

* * * * *

UNITED STATES PATENT AND TRADEMARK OFFICE
CERTIFICATE OF CORRECTION

PATENT NO. : 10,161,883 B2
APPLICATION NO. : 15/757856
DATED : December 25, 2018
INVENTOR(S) : T. Osada et al.

It is certified that error appears in the above-identified patent and that said Letters Patent is hereby corrected as shown below:

In the Claims

At Column 10, Line 5 (Claim 1, Line 12), please change "other the pits" to -- other than the pits --.

Signed and Sealed this
Ninth Day of July, 2019

Andrei Iancu
*Director of the United States Patent and Trademark Office*